US008725699B2

(12) United States Patent
Randazzo et al.

(10) Patent No.: US 8,725,699 B2
(45) Date of Patent: *May 13, 2014

(54) DECISION SUPPORT RESPONSE SYSTEMS AND METHODS

(71) Applicant: General Electric Company, Schenectady, NY (US)

(72) Inventors: Michael Thomas Randazzo, South Jordan, UT (US); Randy Kent Secrist, West Jordan, UT (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/935,113

(22) Filed: Jul. 3, 2013

(65) Prior Publication Data

US 2013/0304490 A1 Nov. 14, 2013

Related U.S. Application Data

(63) Continuation of application No. 11/738,055, filed on Apr. 20, 2007, now Pat. No. 8,510,272.

(51) Int. Cl.
*G06F 7/00* (2006.01)
*G06F 17/00* (2006.01)

(52) U.S. Cl.
USPC .......................................................... 707/687

(58) Field of Classification Search
None
See application file for complete search history.

(56) References Cited

U.S. PATENT DOCUMENTS

| 5,576,952 | A | | 11/1996 | Stutman et al. |
| 5,752,235 | A | * | 5/1998 | Kehr et al. .................... 702/177 |
| 5,942,986 | A | | 8/1999 | Shabot et al. |
| 6,088,677 | A | | 7/2000 | Spurgeon |
| 6,101,478 | A | | 8/2000 | Brown |
| 6,381,577 | B1 | | 4/2002 | Brown |
| 6,470,320 | B1 | | 10/2002 | Hildebrand et al. |

(Continued)

FOREIGN PATENT DOCUMENTS

| EP | 0718784 A1 | 6/1996 |
| JP | 2001212088 | 8/2001 |

(Continued)

OTHER PUBLICATIONS

International Search Report, issued by the European International Searching Authority in connection with International application PCT/US2008/060197, on Jul. 31, 2008, 3 pages.

(Continued)

*Primary Examiner* — Taelor Kim
(74) *Attorney, Agent, or Firm* — Hanley, Flight and Zimmerman, LLC

(57) ABSTRACT

A computer-implemented method for managing data for a clinical decision support system includes providing a computer management system including a server and a database, and downloading the decision support system onto the computer management system. The decision support system includes a plurality of rules and receives data. The method also includes accessing the decision support system and issuing an alert associated with a predetermined data pattern to at least one client system according to the rules, receiving a request for additional information from the at least one client system in response to the issued alert, determining additional data that has been requested, and retrieving the additional information associated with the issued alert.

12 Claims, 3 Drawing Sheets

(56) References Cited

U.S. PATENT DOCUMENTS

| | | | |
|---|---|---|---|
| 7,039,628 | B2 | 5/2006 | Logan et al. |
| 7,251,610 | B2 | 7/2007 | Alban et al. |
| 7,256,708 | B2* | 8/2007 | Rosenfeld et al. ........ 340/870.01 |
| 2003/0135095 | A1* | 7/2003 | Iliff ............................... 600/300 |
| 2003/0172940 | A1* | 9/2003 | Rogers et al. ................. 128/899 |
| 2004/0075433 | A1 | 4/2004 | Kaufman |
| 2004/0130446 | A1 | 7/2004 | Chen et al. |
| 2004/0225199 | A1* | 11/2004 | Evanyk et al. ................ 600/300 |
| 2004/0249250 | A1 | 12/2004 | McGee et al. |
| 2005/0055242 | A1 | 3/2005 | Bello et al. |
| 2005/0108052 | A1* | 5/2005 | Omaboe ........................... 705/2 |
| 2006/0010090 | A1 | 1/2006 | Brockway et al. |
| 2006/0173715 | A1 | 8/2006 | Wang |
| 2006/0230071 | A1 | 10/2006 | Kass et al. |
| 2007/0112782 | A1* | 5/2007 | Lobach et al. .................. 707/10 |
| 2008/0255880 | A1* | 10/2008 | Beller et al. ...................... 705/3 |
| 2009/0187419 | A1 | 7/2009 | Renganathan et al. |
| 2010/0285082 | A1* | 11/2010 | Fernandez ................... 424/422 |

FOREIGN PATENT DOCUMENTS

| | | |
|---|---|---|
| JP | 2002065614 | 3/2002 |
| JP | 2002083066 | 3/2002 |
| JP | 2002245578 | 8/2002 |
| JP | 2002366652 | 12/2002 |
| JP | 2003319913 | 11/2003 |
| JP | 2005190055 | 7/2005 |
| JP | 2006215035 | 8/2006 |
| JP | 2007050247 | 3/2007 |
| JP | 2009075309 | 4/2009 |

OTHER PUBLICATIONS

Final Rejection, issued by the United States Patent and Trademark Office in connection with U.S. Appl. No. 11/738,055, Apr. 15, 2010, 13 pages.

Final Rejection, issued by the United States Patent and Trademark Office in connection with U.S. Appl. No. 11/738,055, Jul. 25, 2012, 17 pages.

Non-final rejection, issued by the United States Patent and Trademark Office in connection with U.S. Appl. No. 11/738,055, Feb. 14, 2012, 14 pages.

Non-final rejection, issued by the United States Patent and Trademark Office in connection with U.S. Appl. No. 11/738,055, Oct. 7, 2009, 11 pages.

Notice of Allowance and Fee(s) Due, issued by the United States Patent and Trademark Office in connection with U.S. Appl. No. 11/738,055, Apr. 3, 2013, 15 pages.

Japan Patent Office, "Office action issued in connection with Japanese patent application No. 2010-504176," with english translation, Nov. 13, 2012, 5 pages.

G.R. Baker, A. MacIntosh-Murray, C. Porcellato, L. Dionne, K. Stelmacovich and K. Born, "Intermountain Healthcare," High Performing Healthcare Systems: Delivering Quality by Design, pp. 151-178, 2008.

Wenke Lee, Gail E. Kaiser, Paul D. Clayton and Eric H. Sherman, "OzCare: A Workflow Automation System for Care Plans," American Medical Informatics Association Annual Fall Symposium, pp. 577-581, 1996.

Peter Porcelli, "A Survey of Neonatal Parenteral Nutrition Design Practices in North Carolina," Journal of Perinatology 24: pp. 137-142, 2004.

* cited by examiner

DECISION SUPPORT RESPONSE SYSTEMS AND METHODS

CROSS-REFERENCE TO RELATED APPLICATIONS

This application claims the benefit of priority to and is a continuation of U.S. patent application Ser. No. 11/738,055, filed Apr. 20, 2007, entitled "Decision Support Response Systems and Methods," which is incorporated by reference in its entirety.

BACKGROUND OF THE INVENTION

This invention relates generally to content management systems and, more particularly to decision support response systems and methods for managing data content using decision support systems of the content management systems.

At least some known content management systems include digital healthcare applications that manage comprehensive clinical, administrative, and/or financial information technology solutions containing integrated and/or interoperable electronic health records. By refining the large amounts of generated clinical related data, some known content management systems provide actionable clinical knowledge at the point of decision. At least some known content management systems include computerized applications such as, but not limited to, physician order entry and/or processing, physician and/or nursing documentation, physician and/or nursing dose charting and/or medication administration record (MAR), accounting, registration, and/or scheduling. Some known content management systems also include hospital information system interfaces, departmental information systems interfaces, and/or interfaces to patient monitoring devices.

Within some known content management systems, some known decision support systems are configured to email alerts and reminders to users based on predetermined data content previously specified by an Administrator. However, upon receipt of an email alert, the users must take an additional step to separately access an associated application to retrieve any other information associated with the email. As a result of the additional step, the users are forced to either permanently and/or temporarily ignore the alert, interrupt a current activity and log into the application to retrieve the additional information, and/or contact another person to retrieve the additional information. As such, known methods for retrieval of clinical related information associated with known automated alerts and reminders is time consuming and/or causes a delay in decision support at the point of care.

BRIEF DESCRIPTION OF THE INVENTION

A computer-implemented method for managing data for a clinical decision support system is provided. The method includes providing a computer management system comprising a server and a database, and downloading the decision support system onto the computer management system. The decision support system includes a plurality of rules and receives data. The method also includes accessing the decision support system and issuing an alert associated with a predetermined data pattern to at least one client system according to the rules, receiving a request for additional information from the at least one client system in response to the issued alert, determining additional data that has been requested, and retrieving the additional information associated with the issued alert.

A decision support system for managing data is provided. The decision support system is configured to issue an alert associated with a predetermined data pattern to at least one client system, receive a request for additional information from at least one client system in response to the issued alert, determine additional data that has been requested, and retrieve the interpreted additional information associated with the issued alert.

A content management system for managing data is provided. The system includes a database for storing the data related to patients, a server operatively coupled to the database, at least one client system operatively coupled to the server, and a decision support system operatively coupled to the server. The decision support system is configured to issue an alert associated with a predetermined data pattern to at least one client system, receive a request for additional information received from at least one client system in response to the issued alert, determine additional data that has been requested, and retrieve the interpreted additional information associated with the issued alert.

DETAILED DESCRIPTION OF THE INVENTION

The methods and systems described herein facilitate retrieval of clinical related information associated with email alerts. The methods and systems described herein are believed to be applicable to many different industries for retrieving many different types of data. Although the exemplary embodiment described herein is the healthcare industry, the invention is in no way limited to the healthcare industry.

Exemplary embodiments of systems and processes that facilitate integrated network-based electronic data entry and workflow process management related to a Content Management System (CMS) for the healthcare industry are described below in detail. The systems and processes facilitate, for example, electronic submission of information using a client system and email alerts for system users. A technical effect of the systems and processes described herein includes permitting a healthcare provider to manage and obtain clinical data. More specifically, in the exemplary embodiment, a healthcare provider such as, but not limited to, a clinician, a physician and/or a nurse utilizes the CMS to manage, track, and retain physician order entry and/or processing, physician and/or nursing documentation, physician and/or nursing dose charting and/or medication administration record (MAR), registration, and/or scheduling related to patients.

Figure 1:
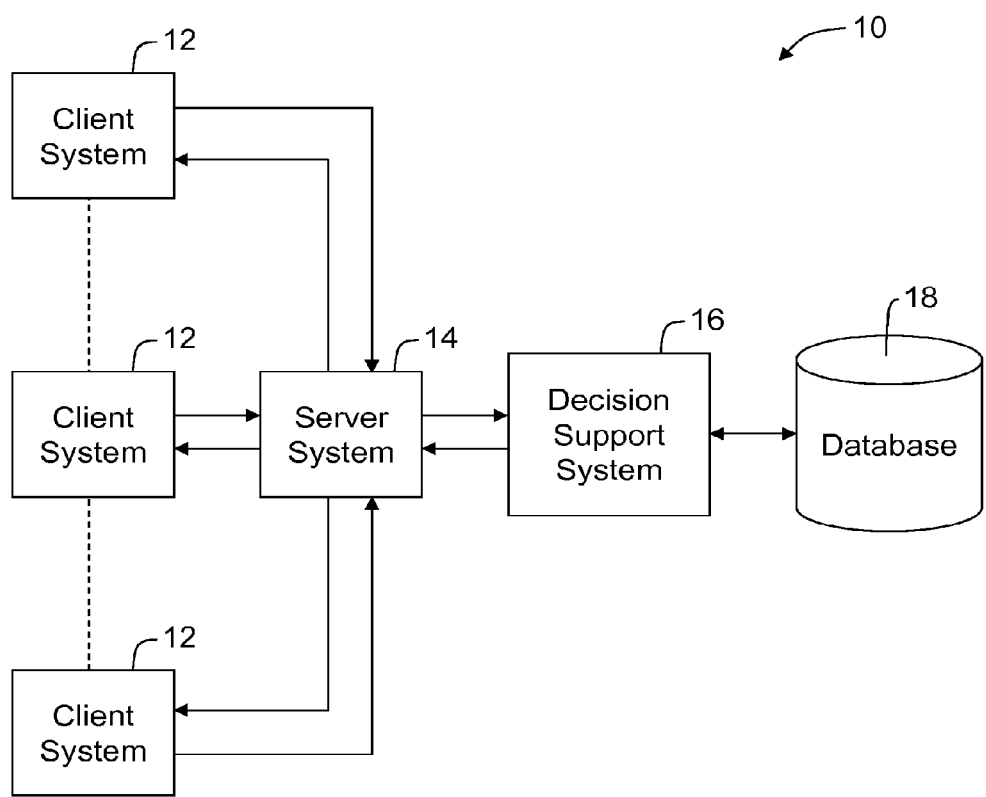
FIG. 1 is a simplified block diagram of an exemplary Content Management System (CMS) including a Decision Support System (DSS)

FIG. 1 is a simplified block diagram of an exemplary Content Management System (CMS) 10 including a plurality of client sub-systems, also referred to as client systems 12, and a server system 14. Client systems 12 include any device capable of interconnecting to the Internet including a web-based phone, a personal digital assistant (PDA), or other web-based connectable devices. In one embodiment, client systems 12 are PDAs including a web browser, such that server system 14 is accessible to client systems 12 using the Internet. Client systems 12 are interconnected to the Internet through many interfaces including a network, such as a local area network (LAN) or a wide area network (WAN), dial-in-connections, cable modems and special high-speed ISDN lines.

CMS 10 also includes a Decision Support System (DSS) 16, which includes a plurality of sub-systems (not shown) and rules configured to track, supply, and retrieve clinically related information based on detected data patterns and/or email alert responses as described below in greater detail. DSS 16 is connected to a centralized database 18 that contains clinically related information. In one embodiment, database 18 is stored on server system 14 and can be accessed by users at one of client systems 12 by logging onto server system 14 through one of client systems 12. In an alternative embodiment, database 18 is stored remotely from server system 14 and may be non-centralized.

Figure 2:
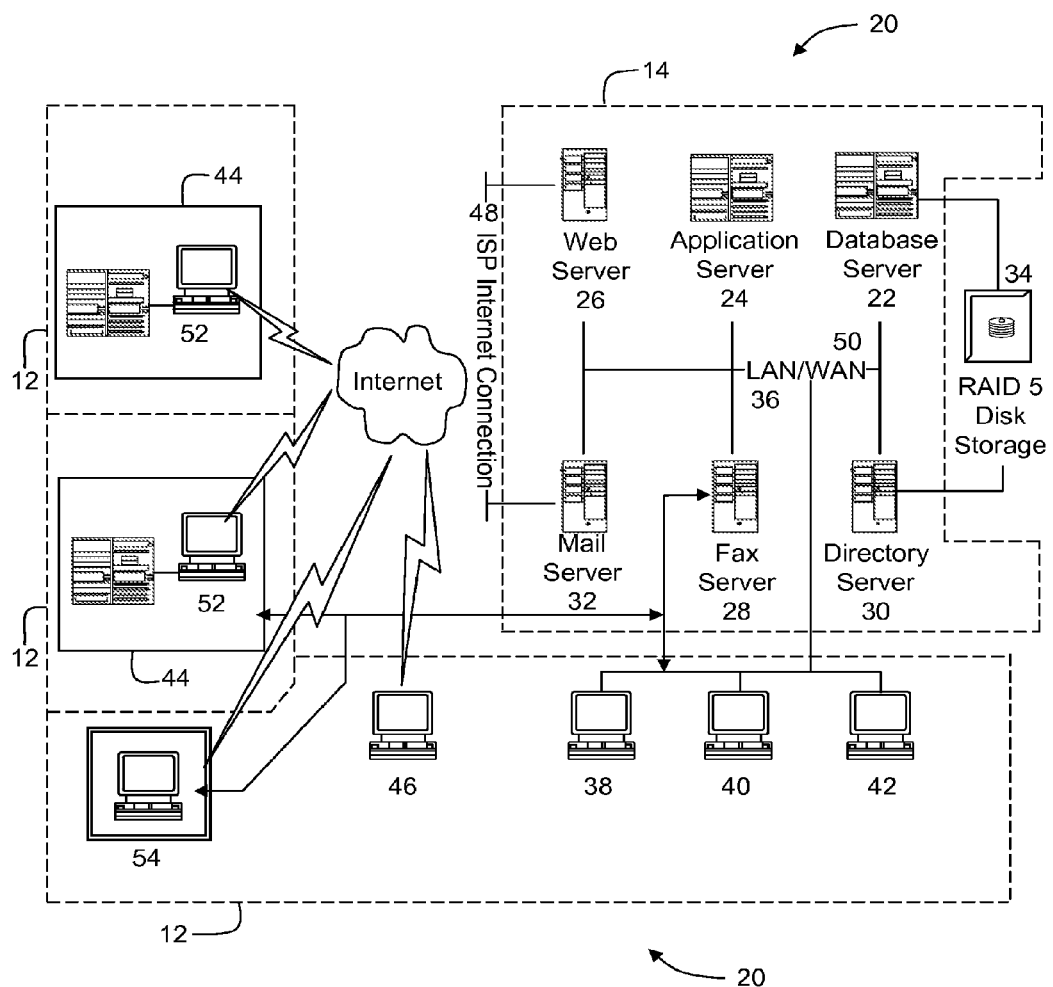
FIG. 2 is an expanded block diagram of a server architecture of the CMS.

FIG. 2 is an expanded block diagram of an exemplary embodiment of a server architecture of CMS 20. Components in CMS 20, identical to components of CMS 10 (shown in FIG. 1), are identified in FIG. 2 using the same reference numerals as used in FIG. 1. CMS 20 includes server system 14 and client systems 12. In one embodiment, server system 14 includes a plurality of conventional servers such as, but not limited to, a database server 22, an application server 24, a web server 26, a fax server 28, a directory server 30, and a mail server 32.

Database server 22 is any database application that manages the processing of data queries by following client/server architecture models to facilitate computer related tasks such as, but not limited to, collecting, displaying, analyzing, storing, retrieving, and/or manipulating data. Application server 24 is a middle-tier software and hardware combination that runs one or more applications to perform a few specific application tasks such as, but not limited to, interpreting site traffic, constructing pages, and/or delivering content to the Web based on a dynamic content repository. Web server 26 is a server that manages, retrieves and/or transfers web based applications over the Internet as they are requested using one or more protocols such as, but not limited to, HTTP and/or FTP. Fax server 28 is a specialized network server that can send, receive, and/or redirect faxes, alphanumeric pages, and/or email messages on a telemessaging platform. Directory server 30 is a server that manages large directories of digital data and provides access to the data that is contained in the directories. Mail server 32 is an application that controls the distribution and storage of email messages. In one embodiment, a disk storage unit 34 is coupled to directory server 30 and database server 22.

Servers 22, 24, 26, 28, 30, and 32 are coupled to a local area network (LAN) 36. In addition, a system administrator's workstation 38, a user workstation 40, and a supervisor's workstation 42 are also coupled to LAN 36. Alternatively, workstations 38, 40, and 42 are coupled to LAN 36 using an Internet link or are connected through an Intranet. Each workstation 38, 40, and 42 is a personal computer having a web browser. Although the functions performed at the workstations typically are illustrated as being performed at respective workstations 38, 40, and 42, such functions can be performed at one of many personal computers coupled to LAN 36. Workstations 38, 40, and 42 are illustrated as being associated with separate functions only to facilitate an understanding of the different types of functions that can be performed by individuals having access to LAN 36.

Server system 14 is configured to be communicatively coupled to various authorized user client systems such as, but not limited to, client systems 44 of physicians and/or client system 46 of nurses that each uses an Internet Service Provider (ISP) Internet connection 48. The communication in the exemplary embodiment is illustrated as being performed using the Internet, however, any other wide area network (WAN) 50 type communication can be utilized in other embodiments, i.e., the systems and processes are not limited to being practiced using the Internet. In the exemplary embodiment, any authorized user having a workstation 52 can access CMS 20. At least one of the client systems 12 includes a manager workstation 54 located at a remote location. Workstations 52 and 54 are personal computers having a web browser and are configured to communicate with server system 14.

Figure 3:
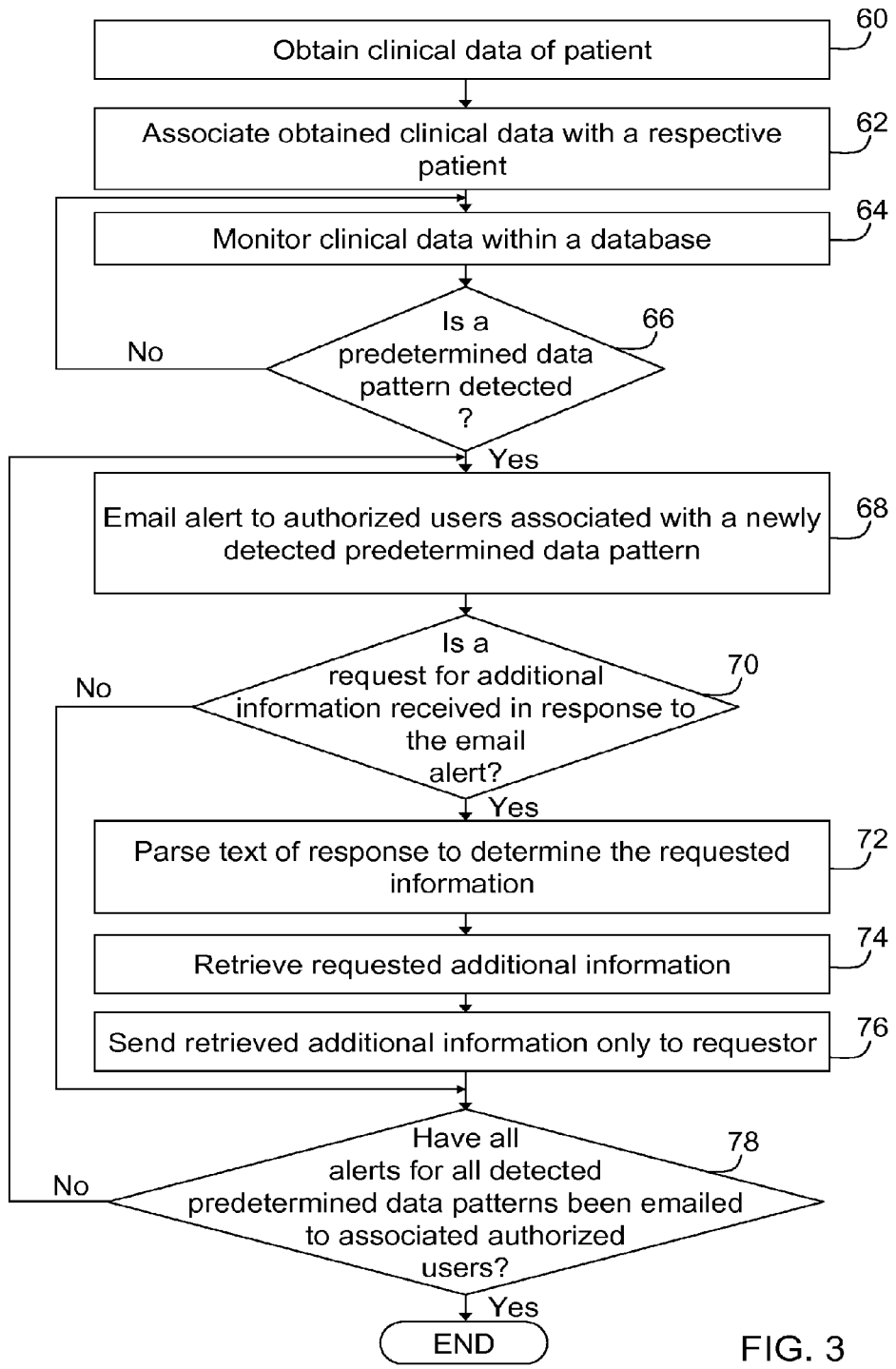
FIG. 3 is a flowchart illustrating exemplary processes utilized in the DSS of the CMS.

FIG. 3 is a flowchart illustrating exemplary processes utilized in DSS 16 of CMS 10 for managing clinical data. Operation of clinical content management performed by DSS 16 begins by obtaining 60 clinical data associated with patients. In the exemplary embodiment, clinical data and/or documents is received and entered into CMS 10 either manually or electronically. Once the clinical data and/or documents have been digitally stored in CMS 10, the information is easily accessed through any computer system or similar device.

In one embodiment, clinical data is collected from any connected data input source such as, but not limited to, a facsimile machine, a scanner, a patient monitor, and/or a multifunctional device. Clinical data is also collected from an application of an authorized healthcare individual such as, but not limited to, physicians, nurses, pharmacists and/or clerks charting patient admission, medication, lab results, and/or any other patient related data. As described previously, clinical data includes any information related to patients such as, but not limited to, lab results, medication orders, vital signs information, physician or nurse documentation, and/or any information that is part of a patient record.

Next, the obtained clinical data is associated 62 with a respective patient. In one embodiment, the obtained clinical data is associated with a unique patient medical record number that is a unique patient identifier such as, for example, a social security number. Additionally, the obtained clinical data is separated into predefined information categories within the respective patient medical record. The obtained clinical data is transferred from DSS 16 to database 18 for storage in database 18 in association with the respective unique patient medical record including any predefined information categories. The information categories are predefined by an application writer.

The stored clinical data within database 18 is monitored 64. It should be appreciated that monitoring cycle of DDS 16 may be a continuous monitoring cycle or a timed monitoring cycle. DSS 16 then determines 66 whether predetermined data patterns have been detected. Data patterns of clinical data are defined by application customers such as, but not limited to, an Administrator associated with a hospital that buys an application. In other words, the Administrator writes general and/or customized rules to look for certain patterns in the clinical data stored in database 18. For example, a predetermined data pattern may include a 5% drop in potassium labs associated with patient medical record numbers stored in database 18.

If no predetermined data patterns are detected, operation returns to monitoring 64 clinical data stored within database 18. If predetermined data patterns are detected, operation continues and an alert is issued 68 and emailed to authorized users associated with a newly detected predetermined data pattern. The subject of the email alert is coded to contain a unique alert identifier for the email alert being sent to the authorized users. The system determines which authorized users should be sent the email alert and the unique patient medical record number associated with the email alert.

Although each email alert may be sent out to multiple authorized users associated with the unique patient medical record number, each alert is associated with a single patient identified by the unique patient medical record number.

Although alerts have been described as email alerts, it should be appreciated that a generated alert may be configurable in any transmittable format such as a pager message. It should also be appreciated that a same alert may be sent to different associated authorized users with different related information. For example, when a predetermined data pattern is detected, an alert may be sent to an associated authorized nurse to indicate that a particular patient in the nurse's unit has low potassium. Based on the detected predetermined pattern, the same alert may be sent to an associated authorized doctor. The alert that is sent to the doctor indicates that the particular patient has low potassium and may provide even more information specifying the exact changes in the potassium labs.

Authorized users that receive the email alert can then reply to the email alert and request additional information from the system. In one embodiment, the alert identifier is left as the subject in requests for additional information by the authorized user email alert recipients. Additionally, the authorized user recipients use keywords in the request for additional information. In one embodiment, keywords are predetermined words and/or syntax specified by an application writer. Authorized users of the application are previously notified, for example, by training of acceptable keywords that are associated with the application.

In addition to encrypting the email alert by conventional methods, the response subject of the authorized user recipient may also be encrypted with a key pair that includes the alert identifier and the user's unique identifier for compliance with the Health Insurance Portability and Accountability Act (HIPAA). DSS 16 then decrypts the message using the authorized recipient user's key pair to facilitate protecting the privacy of electronic clinical data. For example, encryption adds conventional electronic signatures so that only an intended recipient can read the electronic document. The electronic signatures may include a digital certificate as a form of credentials used in conjunction with encryption to verify that the individual sending information electronically is being truthful about his/her identity. By using encryption or any other known security mechanism to verify the identity of authorized users, any verification device connected to DSS 16 facilitates securing access to and/or transmission of confidential clinical data.

DSS 16 determines 70 whether a request for additional information has been received in response to the emailed alert. If a request for additional information is determined 70, operation continues and text associated with the response is parsed 72 to determine acceptable predetermined keywords that identify the requested information. DSS 16 then retrieves 74 additional requested information from database 18. DSS 16 sends 76 the requested additional information through server system 14. Although each email alert may be sent out to multiple authorized users associated with the unique patient medical record number, in one embodiment, requested information is sent only to the requesting authorized user. However, the requesting authorized user may forward the additional requested information to another authorized individual such as the patient's nurse.

If a request for additional information is not determined 70, DSS 16 determines 78 whether all alerts for all detected predetermined data patterns have been emailed to associated authorized users. If all alerts for all detected predetermined data patterns have not been emailed, operation returns to issue 68 any unissued alerts. If all alerts for all detected predetermined data patterns have been emailed, operation ends.

During operation of the methods and systems described above, for example, an authorized doctor receives an email alert. However, the doctor may not be able to log into an application to look at the clinical data associated with the email alert. For example, the doctor may not be in the hospital when the alert is received or the doctor may not have access to a device that can open applications associated with the patient electronic medical record. The doctor can respond to the email alert to request additional information associated with the alert without having to log into the system and then make a determination as to a course of action to be taken such as, but not limited to, determining whether an application should be opened to access more clinical data for the associated patient medical record.

It should be appreciated that although the example discussed above is related to the heath care industry, the CMS system may be used in any other business or field of endeavor involving records and documentation. For example, the CMS system can also be used in the financial industry including the phases of tracking market patterns for a product and/or service. Further, it should be appreciated that the systems and processes are not limited to the specific embodiments described herein. In addition, components of each system and each process can be practiced independently and separately from other components and processes described herein. Each component and process also can be used in combination with other assembly packages and processes.

In the exemplary embodiment, content management system (CMS) 10 is configured to allow authorized users to interact with the system using email. In particular, CMS 10 is configured to receive email alerts and respond to the alert to request additional information. CMS 10 includes a decision support system (DSS) 16 that is configured to detect predetermined data patterns, issue an email alert, receive and interpret a responsive email that requests additional information associated with the issued email alert, retrieve the requested information, and transmit that information to the requester.

As a result, additional information associated with an alert may be retrieved without opening an associated application. As such, authorized associated users receiving an email alert have the ability to interact with the decision support system through email to retrieve further information before deciding if another individual needs to be contacted and/or if the authorized associated users should interrupt what they are doing and go see the patient. Additionally, the authorized associated users that request additional information may continue what they are currently doing while waiting for receipt of the requested additional information. Also, giving authorized associated users the ability to query additional data from any location facilitates providing faster user responses and more information for users to make informed decisions.

Exemplary embodiments of methods and systems for managing clinical data are described in detail above. The methods and systems are not limited to the specific embodiments described herein or to the specific illustrated content management and decision support methods and systems.

While the invention has been described in terms of various specific embodiments, those skilled in the art will recognize that the invention can be practiced with modification within the spirit and scope of the claims.

What is claimed is:

1. A computer-implemented method comprising:

analyzing, using a clinical decision support system, clinical data to detect a predetermined data pattern for a patient, the patient associated with a patient identifier and the clinical data arranged according to one or more information categories;

issuing an alert associated with the predetermined data pattern, the issued alert associated with an alert identifier and sent as a first message to an authorized user;

receiving, from the authorized user receiving the alert, a second message in reply to the first message, the second message to trigger a request for information relating to the patient and the predetermined data pattern based on the alert identifier and the patient identifier;

parsing the second message based on one or more keywords to identify the information requested by the authorized user in the second message;

retrieving, in response to the second message, the information requested by the authorized user; and transmitting the information requested in a third message to the authorized user, wherein the information requested is reviewable by the authorized user via the third message, wherein at least one of the first, second and third messages comprises an email message, and wherein the authorized user interacts with the clinical decision support system via the messages without opening a clinical decision support system application.

2. A method in accordance with claim 1, wherein a clinical decision support system is to provide rules to track, identify, and retrieve clinically related information based on detected data patterns and messages.

3. A method in accordance with claim 1, wherein issuing further comprises coding the alert based on the alert identifier that identifies the issued alert and associates the issued alert with the patient identifier.

4. A method in accordance with claim 1, wherein at least one of the first, second and third messages is to be verified based on the authorized user's user identifier.

5. A clinical decision support system comprising a processor and memory configured to:

analyze clinical data to detect a predetermined data pattern for a patient, the patient associated with a patient identifier and the clinical data arranged according to one or more information categories;

issue an alert associated with the predetermined data pattern, the issued alert associated with an alert identifier and sent as a first message to an authorized user;

receive, from the authorized user receiving the alert, a second message in reply to the first message, the second message to trigger a request for information relating to the patient and the predetermined data pattern based on the alert identifier and the patient identifier;

parse the second message based on one or more keywords to identify the information requested by the authorized user in the second message;

retrieve, in response to the second message, the information requested by the authorized user; and transmit the information requested in a third message to the authorized user, wherein the information requested is reviewable by the authorized user via the third message, wherein at least one of the first, second and third messages comprises an email message, and wherein the authorized user interacts with the clinical decision support system via the messages without opening a clinical decision support system application.

6. A system in accordance with claim 5, wherein the clinical decision support system is to provide rules to track, identify, and retrieve clinically related information based on detected data patterns and messages.

7. A system in accordance with claim 5, wherein issuing further comprises coding the alert based on the alert identifier that identifies the issued alert and associates the issued alert with the patient identifier.

8. A system in accordance with claim 5, wherein at least one of the first, second and third messages is to be verified based on the authorized user's user identifier.

9. A non-transitory computer readable storage medium including a set of instructions which, when executed, implement a content management system to manage clinically related data, the content management system configured to:

analyze clinical data to detect a predetermined data pattern for a patient, the patient associated with a patient identifier and the clinical data arranged according to one or more information categories;

issue an alert associated with the predetermined data pattern, the issued alert associated with an alert identifier and sent as a first message to an authorized user;

receive, from the authorized user receiving the alert, a second message in reply to the first message, the second message to trigger a request for information relating to the patient and the predetermined data pattern based on the alert identifier and the patient identifier;

parse the second message based on one or more keywords to identify the information requested by the authorized user in the second message;

retrieve, in response to the second message, the information requested by the authorized user; and transmit the information requested in a third message to the authorized user, wherein the information requested is reviewable by the authorized user via the third message, wherein at least one of the first, second and third messages comprises an email message, and wherein the authorized user interacts with the content management system via the messages without opening a content management system application.

10. A non-transitory computer readable storage medium in accordance with claim 9, wherein the content management system is to provide rules to track, identify, and retrieve clinically related information based on detected data patterns and messages.

11. A non-transitory computer readable storage medium in accordance with claim 9, wherein issuing further comprises coding the alert based on the alert identifier that identifies the issued alert and associates the issued alert with the patient identifier.

12. A non-transitory computer readable storage medium in accordance with claim 9, wherein at least one of the first, second and third messages is to be verified based on the authorized user's user identifier.

* * * * *